(12) United States Patent
Galli et al.

(10) Patent No.: US 6,835,730 B2
(45) Date of Patent: Dec. 28, 2004

(54) 4-HETEROPARYL-1,4-DIAZABICYCLO[3.2.2] NONANE, PREPARATION AND THERAPEUTIC USE THEREOF

(75) Inventors: Frédéric Galli, Vaucresson (FR); Samir Jegham, Montferrier-sur-Lez (FR); Odile Leclerc, Briis sous Forges (FR); Alistair Lochead, Charenton-le-Pont (FR); Alain Nedelec, Colombes (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/181,870

(22) PCT Filed: Jan. 24, 2001

(86) PCT No.: PCT/FR01/00227
§ 371 (c)(1),
(2), (4) Date: Sep. 24, 2002

(87) PCT Pub. No.: WO01/55150
PCT Pub. Date: Aug. 2, 2001

(65) Prior Publication Data
US 2003/0119840 A1 Jun. 26, 2003

(30) Foreign Application Priority Data
Jan. 28, 2000 (FR) .............................. 00 01098

(51) Int. Cl.⁷ ................... C07D 487/08; A61K 31/551
(52) U.S. Cl. ..................................... 514/221; 540/556
(58) Field of Search ................................. 514/221; 540/556

(56) References Cited

U.S. PATENT DOCUMENTS 5,478,939 A  12/1995  Trybulski et al. ............ 544/336
6,407,095 B1  6/2002  Lochead et al. ............ 514/221

FOREIGN PATENT DOCUMENTS

WO  WO 00/34279  6/2000
WO  WO 00/34284  6/2000

OTHER PUBLICATIONS

Derwent Patent Abstract No. 200036 (2002).

Primary Examiner—Bruck Kifle
(74) Attorney, Agent, or Firm—Michael D. Alexander

(57) ABSTRACT

Compounds of the general formula (I)

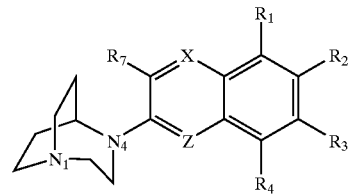

in which $R_1$, $R_2$, $R_3$ and $R_4$ each represent a hydrogen or halogen atom or a nitro, amino, trifluoromethyl, cyano, hydroxyl, alkyl or alkoxy group, X represents either a nitrogen atom, in which case Z represents a group of the formula C—$R_5$ or a nitrogen atom, or a group of the formula C—$R_6$, in which case Z represents a nitrogen atom, $R_5$ and $R_6$ each represent a hydrogen or halogen atom or a trifluoromethyl, cyano, hydroxyl, ($C_1$–$C_6$)alkyl or ($C_1$–$C_6$) alkoxy group, and $R_7$ represents a hydrogen atom or a ($C_1$–$C_6$)alkyl group.

Use in therapy.

3 Claims, No Drawings

4-HETEROPARYL-1,4-DIAZABICYCLO[3.2.2] NONANE, PREPARATION AND THERAPEUTIC USE THEREOF

The present invention relates to compounds which correspond to the general formula (I)

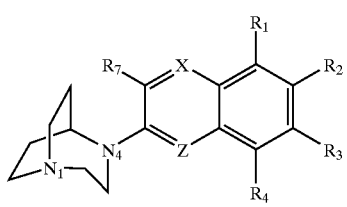

(I)

in which $R_1$, $R_2$, $R_3$ and $R_4$ each represent, independently of each other, a hydrogen or halogen atom or a nitro, amino, trifluoromethyl, cyano, hydroxyl, (C1–C6)alkyl or ($C_1$–$C_6$)alkoxy group, X represents
either a nitrogen atom, in which case Z represents a group of the formula C—$R_5$ or a nitrogen atom,
or a group of the formula C—$R_6$, in which case Z represents a nitrogen atom, $R_5$ and $R_6$ each represent, independently of each other, a hydrogen or halogen atom or a trifluoromethyl, cyano, hydroxyl, ($C_1$–$C_6$)alkyl or ($C_1$–$C_6$)alkoxy group, and $R_7$ represents a hydrogen atom or a ($C_1$–$C_6$)alkyl group.

The compounds of the invention can exist as bases or as acid addition salts.

In accordance with the invention, it is possible to prepare the compounds of the general formula (I) by a process which is illustrated by the scheme which follows.

1,4-Diazabicyclo[3.2.2]nonane of the formula (II) is reacted with a heterocyclic compound of the general formula (III) in which $R_1$, $R_2$, $R_3$, $R_4$, $R_7$, X and Z are as defined above and W represents a halogen atom. In this way, it is possible to perform a Buchwald-type coupling reaction (*J. Org. Chem.* 1997, 62, 6066–6068) in the presence of a palladium catalyst, such as palladium acetate, tris (dibenzylideneacetone)-dipalladium (0), etc., of a complexing ligand such as triphenylphosphine, tributylphosphine or 2,2'-bis(di-phenylphosphino)-1,1'-binaphthyl, and of a base, for example an organic base, such as sodium tert-butoxide, or an inorganic base, such as cesium carbonate.

Scheme

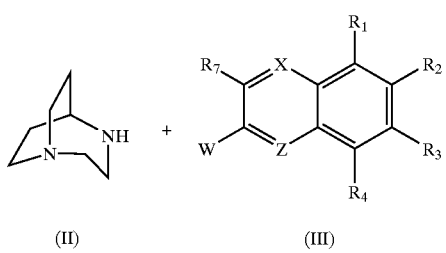

It is also possible to carry out a nucleophilic substitution reaction in the presence of a strong base such as cesium carbonate or triethylamine.

The preparation of 1,4-diazabicyclo[3.2.2]-nonane is described in *J. Med. Chem.* 1993, 36, 2311–2320.

The compounds of the general formula (III) are either commercially available or can be obtained by methods which are described in the literature.

The examples which follow illustrate the preparation of some compounds of the invention. The elemental microanalyses and the IR and NMR spectra confirm the structures of the compounds which are obtained. The numbers indicated in brackets in the titles of the examples correspond to those of the 1st column of the table which is presented further below. In the names of the compounds, the hyphen "-" is part of the word and the hyphen "_" is only used for the break at the end of a line; it is not to be used in the absence of any break and should not be replaced either by a normal hyphen or by a space.

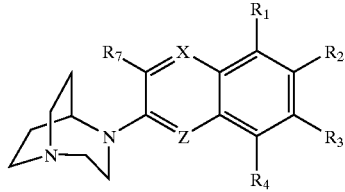

(I)

EXAMPLE 1

Compound No. 1

4-(Quinolin-3-yl)-1,4-diazabicyclo[3.2.2]nonane Hydrobromide 2:1

2.3 g (18 mmol) of 1,4-diazabicyclo[3.2.2]_nonane, 11.3 g (55 mmol) of 3-bromoquinoline, 8.3 g (25 mmol) of cesium carbonate, 0.164 g (0.73 mmol) of palladium diacetate and 0.454 g (0.73 mmol) of 2,2'-bis (diphenylphosphino)-1,1'-binaphthyl, in solution in 180 ml of tetrahydrofuran, are introduced consecutively into a 500 ml three-necked round-bottomed flask and the reaction mixture is heated at reflux for 22 h. The mixture is filtered through kieselguhr and the solvent is evaporated under reduced pressure; the residue is purified by chromatography on a silica gel column, with the elution being carried out using a 95/5/0.5 mixture of dichloromethane, methanol and ammonia.

0.83 g of an oily product is obtained, with this product being treated with 1.15 ml of a 5.7 M solution of hydrobromic acid in acetic acid and with the crystals which are obtained being recrystallized in a mixture of ethanol and methanol.

Melting point: 309–316° C.

EXAMPLE 2

Compound No. 2

4-(8-Nitroquinolin-3-yl)-1,4-diazabicyclo[3.2.2]nonane.

2.1 3-Bromo-8-nitroquinoline.

10 g (57 mmol) of 8-nitroquinoline, in solution in 100 ml of acetic acid, are introduced into a 500 ml three-necked round-bottomed flask, after which 11.3 g (63 mmol) of N-bromosuccinimide are added and the mixture is heated at 100–110° C. for 6 h. After it has been cooled down to room temperature, the reaction medium is poured into 300 ml of water and the precipitate is collected by filtration; it is rinsed with water and dried in vacuo. The residue is purified by chromatography on a silica gel column, with the elution being carried out using a 50/50, and then a 70/30, mixture of dichloromethane and cyclohexane. 12.3 g of product are obtained.

Melting point: 123–124° C.

2.2 4-(8-Nitroquinolin-3-yl)-1,4-diazabicyclo[3.2.2]_nonane.

1.54 g (6.1 mmol) of 3-bromo-8-nitro_quinoline, 0.7 g (5.5 mmol) of 1,4-diazabicyclo_[3.2.2]nonane, 0.05 g (0.22 mmol) of palladium diacetate, 2.5 g (7.7 mmol) of cesium carbonate and 0.137 g (0.22 mmol) of 2,2'-bis (diphenylphosphino)-1,1'-binaphthyl, in 30 ml of tetrahydrofuran and 10 ml of toluene, are introduced consecutively into a 100 ml three-necked round-bottomed flask and the reaction mixture is heated at 80–90° C. for 24 h. The inorganic products are separated by filtration and the solvent is evaporated under reduced pressure. The residue is purified by chromatography on a silica gel column, with the elution being carried out using a 95/5/0.5, and then a 90/10/1, mixture of dichloromethane, methanol and ammonia. 1.18 g of solid are obtained, with this solid then being recrystallized in methanol.

Melting point: 180–181° C.

EXAMPLE 3

Compound No. 6
4-(8-Aminoquinolin-3-yl)-1,4-diazabicyclo[3.2.2]nonane.

0.8 g (2.7 mmol) of 4-(8-nitroquinolin-3-yl)-1,4-diazabicyclo[3.2.2]nonane, in suspension in a mixture of 8 ml of water and 4 ml of acetic acid, is introduced into a 25 ml three-necked round-bottomed flask and the suspension is heated at 40° C.; 0.43 g (7.7 mmol) of iron are then added, in two portions, and the mixture is heated at 50° C. for 1 h.

It is then cooled down to room temperature and filtered through kieselguhr; the solvent is evaporated under reduced pressure and the residue is purified by chromatography on a silica gel column, with the elution being carried out using a 90/10/1 mixture of dichloromethane, methanol and ammonia.

0.18 g of a yellow oil, which crystallizes, is obtained.

Melting point: 149–152° C.

EXAMPLE 4

Compound No. 5
4-(6-Chloroquinolin-3-yl)-1,4-diazabicyclo[3.2.2]_nonane.
4.1 3-Bromo-6-chloroquinoline.

4.8 g (29 mmol) of 6-chloroquinoline, in solution in 50 ml of acetic acid, are introduced into a 100 ml three-necked round-bottomed flask, after which 5.75 g (32 mmol) of N-bromosuccinimide are added and the mixture is heated at 100° C. for 6 h. The reaction mixture is poured into 100 ml of water and the whole is extracted with dichloromethane. The pooled organic phases are dried over magnesium sulfate and concentrated under reduced pressure. The residue is purified by chromatography on a silica gel column, with the elution being carried out using a 50/50, and then a 30/70, mixture of cyclohexane and dichloromethane.

4.86 g of product are obtained.

Melting point: 110–111° C.

4.2 4-(6-Chloroquinolin-3-yl)-1,4-diazabicyclo[3.2.2]_nonane 0.53 g (2.18 mmol) of 3-bromo-6-chloro_quinoline, 0.25 g (2 mmol) of 1,4-diazabicyclo[3.2.2]_nonane, 0.018 g (0.08 mmol) of palladium diacetate, 0.91 g (2.8 mmol) of cesium carbonate and 0.05 g (0.08 mmol) of 2,2'-bis (diphenylphosphino)-1,1'-bi_naphthyl, in 15 ml of tetrahydrofuran, are introduced consecutively into a 50 ml three-necked round-bottomed flask and the reaction mixture is heated at reflux for 26 h.

The inorganic products are separated off by filtration and the solvent is evaporated under reduced pressure; the residue is then purified by chromatography on a silica gel column, with the elution being carried out using a 95/5/0.5, and then a 90/10/1, mixture of dichloromethane, methanol and ammonia.

0.40 g of solid is obtained, with this solid being recrystallized in diisopropyl ether.

Melting point: 134–135° C.

EXAMPLE 5

Compound No. 9
4-(6-Quinolin-2-yl)-1,4-diazabicyclo[3.2.2]nonane hydrobromide 1:1.

0.83 g (6.58 mmol) of 1,4-diazabicyclo_[3.2.2]nonane and 1.08 g of 2-chloroquinoline, in solution in 30 ml of toluene, are introduced into a 100 ml three-necked round-bottomed flask and the mixture is heated at reflux for 72 h.

The solution is concentrated under reduced pressure and the residue is purified by chromatography on a silica gel column, with the elution being carried out using a 95/5/0.5, and then a 90/10/1, mixture of dichloromethane, methanol and ammonia.

0.24 g of an oily product is obtained; this product is dissolved in isopropyl alcohol before adding 0.17 ml of a 5.7 N solution of hydrobromic acid in acetic acid. After cooling, the crystals which are obtained are collected by filtration and are dried in vacuo. Melting point: 253–255° C.

The table which follows illustrates the chemical structures and the physical properties of some compounds of the invention.

TABLE (I)

| No. | $R_1$ | $R_2$ | $R_3$ | $R_4$ | $R_7$ | X | Z | Salt | M.p. (° C.) |
|---|---|---|---|---|---|---|---|---|---|
| 1 | H | H | H | H | H | N | CH | HBr 2:1 | 309–316 |
| 2 | $NO_2$ | H | H | H | H | N | CH | — | 180–181 |
| 3 | H | H | $NO_2$ | H | H | N | CH | — | 195–197 |
| 4 | Cl | H | H | H | H | N | CH | — | 124–125 |
| 5 | H | H | Cl | H | H | N | CH | — | 134–135 |
| 6 | $NH_2$ | H | H | H | H | N | CH | — | 149–152 |
| 7 | H | H | $NH_2$ | H | H | N | CH | — | 183–184 |
| 8 | $CH_3$ | H | H | H | H | N | CH | HBr 2:1 | 295–303 |
| 9 | H | H | H | H | H | CH | N | HBr 1:1 | 253–255 |
| 10 | H | H | H | H | H | N | N | HBr 1:1 | 317–318 |
| 11 | H | H | H | H | $CH_3$ | CH | N | HBr 2:1 | 238–241 |
| 12 | H | H | H | H | H | $CCH_3$ | N | HBr 3:1 | 231–233 |
| 13 | Cl | $OCH_3$ | H | H | H | CH | N | — | 176–178 |
| 14 | $NO_2$ | $CH_3$ | H | H | H | CH | N | HBr 2:1 | 254–256 |
| 15 | H | Cl | H | H | H | CH | N | HBr 2:1 | >300 (d) |
| 16 | H | H | $CH_3$ | H | H | CH | N | HBr 2:1 | 292–294 |
| 17 | $NO_2$ | H | H | H | H | CH | N | HBr 2:1 | 318–321 |
| 18 | $NO_2$ | $CF_3$ | H | H | H | CH | N | HBr 3:1 | 321–323 |
| 19 | $NH_2$ | H | H | H | H | CH | N | HBr 2:1 | 329–331 |
| 20 | H | $OCH_3$ | H | H | H | CH | N | HBr 2:1 | 284–285 |
| 21 | H | $CF_3$ | H | H | H | CCl | N | HBr 2:1 | 325–326 |
| 22 | H | H | $CH_3$ | $NO_2$ | H | CH | N | HBr 2:1 | >370 (d) |
| 23 | H | H | H | H | H | CCl | N | — | 106–107 |
| 24 | H | H | $CF_3$ | H | H | CCl | N | HBr 2:1 | 309–311 |
| 25 | H | H | H | $CH_3$ | H | CH | N | HBr 2:1 | 298–300 |
| 26 | H | $CH_3$ | H | H | H | CH | N | HBr 2:1 | >300 (d) |
| 27 | H | $NO_2$ | H | H | H | CH | N | HBr 2:1 | 223–224 |

In the "Salt" column, "-" designates a compound which is in the form of a base and "HBr" designates a hydrobromide; the acid:base molar ratio is indicated alongside.

In the "M.p. (° C.)" column, "(d)" indicates a melting temperature with decomposition.

The compounds of the invention were subjected to biological tests, which demonstrated the importance of the compounds as substances which can be used for therapeutic purposes.

Thus, they were studied with regard to their affinity for nicotinic receptors containing the $\alpha_4\beta_2$ subunit using methods described by Anderson and Arneric in *Eur. J. Pharmacol.* 1994, 253, 261 and by Hall et al. in *Brain Res.* 1993, 600, 127.

Male Sprague Dawley rats weighing 150 to 200 g are decapitated and the whole brain is removed rapidly and homogenized, at 4° C., in 15 volumes of a 0.32 M sucrose solution, with this homogenate then being centrifuged at 1 000 g for 10 min. The pellet is discarded and the supernatant is centrifuged at 20 000 g and 4° C. for 20 min. The pellet is recovered and homogenized, at 4° C., in 15 volumes of double-distilled water using a Polytron™ mill; the homogenate is then centrifuged at 8 000 g for 20 min. The pellet is discarded and the supernatant and the buffy coat are centrifuged at 40 000 g for 20 min; the pellet is recovered and resuspended in 15 ml of double-distilled water and centrifuged once again at 40 000 g before being stored at −80° C.

On the day of the experiment, the tissue is thawed slowly and suspended in 3 volumes of buffer. 150 µl of this membrane suspension are incubated, at 4° C. for 120 min, in the presence of 100 µl of 1 nM [$^3$H]-cytisine in a final volume of 500 µl of buffer and in the presence or absence of the compound to be tested. The reaction is stopped by filtering through Whatman GF/B™ filters which have been previously treated with polyethylenimine. The filters are rinsed, at 4° C., with two times 5 ml of buffer and the radioactivity which is retained on the filter is measured by liquid scintillation counting. The nonspecific binding is determined in the presence of 10 µM (−)-nicotine; the nonspecific binding represents from 75 to 85% of the total binding recovered on the filter. The percentage inhibition of the specific binding of [3H]-cytisine is determined for each concentration of the compound studied and the $IC_{50}$, i.e. the concentration of the compound which inhibits the specific binding by 50%, is then calculated. The $IC_{50}$ values for the compounds of the invention having the highest affinity lie between 0.003 and 0.012 µM.

The compounds of the invention were also studied with regard to their affinity for nicotinic receptors containing the $\alpha_7$ subunit using the methods described by Mark and Collins in *J. Pharmacol. Exp. Ther.* 1982, 22, 564 and by Marks et al. in *Mol. Pharmacol.* 1986, 30, 427.

Male OFA rats weighing from 150 to 200 g are decapitated and the whole brain is removed rapidly and homogenized, at 4° C., in 15 volumes of an 0.32 M sucrose solution using a Polytron™ mill; the homogenate is then centrifuged at 1 000 g for 10 min. The pellet is discarded and the supernatant is centrifuged at 8 000 g and 4° C. for 20 min. The pellet is recovered and homogenized, at 4° C., in 15 volumes of double-distilled water using a Polytron™ mill; the homogenate is then centrifuged at 8 000 g for 20 min. The pellet is discarded and the supernatant and the buffy coat are centrifuged at 40 000 g for 20 min. The pellet is recovered and resuspended, at 4° C., in 15 volumes of double-distilled water and then centrifuged once again at 40 000 g for 20 min before being stored at −80° C. On the day of the experiment, the tissue is thawed slowly and suspended in 5 volumes of buffer. 150 μl of this membrane suspension are preincubated in the dark, at 37° C. for 30 min, in the presence or absence of the compound to be tested. The membranes are then incubated in the dark, at 37° C. for 60 min, in the presence of 50 μl of 1 nM [3H]-α-bungarotoxin in a final volume of 250 μl of 20 nM HEPES buffer, 0.05% polyethylenimine. The reaction is stopped by filtering through Whatman GF/C™ filters which have been previously treated for 3 h with 0.05% polyethylenimine. The filters are rinsed, at 4° C., with two times 5 ml of buffer and the radioactivity retained on each filter is measured by liquid scintillation counting. The nonspecific binding is determined in the presence of a final α-bungarotoxin concentration of 1 μM; the nonspecific binding represents approximately 60% of the total binding recovered on the filter. The percentage inhibition of the specific binding of [$^3$H]-α-bungarotoxin is determined for each concentration of the compound studied and the $IC_{50}$, i.e. the concentration of the compound which inhibits the specific binding by 50%, is then calculated.

The $IC_{50}$ values of the compounds of the invention having the highest affinity lie between 0.022 and 5.5 μM.

The above results show that certain compounds of the invention are selective ligands for the $α_4β_2$ or $α_7$ subunits of the nicotinic receptor while others are mixed $α_4β_2$ and $α_7$ ligands.

Finally, the compounds of the invention were subjected to tests which demonstrated the analgesic properties of these compounds. Thus, the compounds were studied in the hotplate model, using the method described by Eddy and Leimbach in *J. Pharmacol. Exp. Ther.* 1953, 107, 385, with the aim of looking for, and quantifying, any possible analgesic effect.

Mice weighing from 20 to 30 g are subjected to a thermal stimulus by bringing their paws into contact with a plate which is maintained at a constant temperature of 57.5° C. by means of a thermostated waterbath. The time taken for a reaction to the pain to occur, which reaction is manifested by licking of the paws or by a jump, is measured. Thus, after the time for pretreatment, which is effected subcutaneously or orally (each batch consisting of eight animals for one and the same pretreatment), the mice are placed individually on the plate and the time taken to react to the pain is measured. The animal is removed from the plate immediately after the pain has been manifested. The maximum time of exposure to the stimulus is 30 seconds. The mean reaction time, together with the standard error of the mean (s.e.m.) is calculated for each batch. A non-parametric analysis of variance (Kruskal-Wallis) is carried out on the entire batch. A Wilcoxon test enables each treated batch to be compared with the control batch. The differences are regarded as being statistically significant at the 5% threshold. This reaction time is significantly increased by analgesics which chiefly affect the central nervous system.

In this test, the compounds of the invention exhibit an activity at doses of between 0.3 and 100 mg/kg when administered by the subcutaneous or oral route.

The results of the various tests provide support for using the compounds in the treatment or prevention of disorders which are linked to dysfunction of the nicotinic receptors, in particular at the level of the central nervous system or of the gastrointestinal system.

At the level of the central nervous system, these disorders comprise cognitive changes, more specifically amnesic, but also attentional, changes, which are linked to Alzheimer's disease, to pathological aging (age-associated memory impairment, AAMI), to the Parkinsonian syndrome, to trisomy 21 (Down's syndrome), to Korsakoff's alcoholic syndrome, to vascular dementias (multi-infarct dementia, MDI), and to attention deficits/hyperactivity (ADHA). It would also be possible for the compounds of the invention to be used in the treatment of the motor disorders which are observed in Parkinson's disease or other neurological diseases such as Huntington's chorea, Tourette's syndrome, tardive dyskinesia and hyperkinesia.

The compounds of the invention can also constitute a symptomatic and/or etiological treatment for acute or chronic neurodegenerative diseases. They can be used in psychiatric disorders: schizophrenia, depression, anxiety, panic attacks and compulsive and obsessional behaviour. They can prevent the symptoms which are due to being deprived of tobacco and alcohol and various substances which induce dependence such as cocaine, LSD, cannabis and benzodiazepines.

Finally, they can be used for the treatment of pain. At the level of the gastrointestinal system, the compounds of the invention can be used for treating Crohn's disease, ulcerative colitis, irritable bowel syndrome and obesity.

Thus, the present invention also relates to pharmaceutical compositions which comprise an effective dose of at least one compound according to the invention, as a pharmaceutically acceptable base, salt or solvate, which is mixed, where appropriate, with suitable excipients.

Said excipients are selected in accordance with the pharmaceutical form and desired mode of administration. The pharmaceutical compositions according to the invention can thus be intended for oral, sublingual, subcutaneous, intramuscular, intravenous, topical, intratracheal, intranasal, transdermal, rectal or intraocular administration.

The unit forms of administration may, for example, be tablets, gelatin capsules, granules, powders, oral or injectable solutions or suspensions, patches or suppositories. For topical administration, it is possible to envisage ointments, lotions and eye drops. Said unit forms are dosed in order to make it possible to administer from 0.01 to 20 mg of active substance per kg of body weight per day.

In order to prepare tablets, a pharmaceutical excipient, which can be composed of extenders, such as lactose, microcrystalline cellulose or starch, and formulation adjuvants, such as binding agents (polyvinylpyrrolidone, hydroxypropylmethyl cellulose, etc.), flowance agents, such as silica, and lubricants, such as magnesium stearate, stearic acid, glycerol tribehenate or sodium stearylfumarate, are added to the active substance, which is or is not micronized. Wetting agents or surfactants, such as sodium lauryl sulfate, can also be added.

The techniques used for preparing the tablets may be direct compression, dry granulation, wet granulation or hot melt. The tablets can be uncoated, sugar-coated, for example with sucrose, or coated with a variety of polymers or other appropriate materials. They can be designed in order to permit rapid, delayed or prolonged release of the active substance by virtue of polymeric matrices or of specific polymers which are employed in coating.

In order to prepare gelatin capsules, the active substance is mixed with dry (simple mixture, dry or wet granulation, or hot melt), liquid or semisolid pharmaceutical excipients.

The gelatin capsules can be hard or soft and film-covered or not, so as to have a rapid, prolonged or delayed (for example in the case of an enteric form) activity.

A composition in the form of a syrup or elixir, or for administration in the form of drops, can contain the active substance conjointly with a sweetener, which is preferably calorie-free, methylparaben or propylparaben, as antiseptic agent, a flavour-modifying agent and a dye.

The powders and granules which are dispersible in water can contain the active substance mixed with dispersing agents or wetting agents, or dispersing agents such as polyvinylpyrrolidone, as well as with sweeteners and taste corrigents.

For rectal administration, use is made of suppositories which have been prepared using binding agents which melt at rectal temperature, for example cocoa butter or polyethylene glycols.

For parenteral administration, use is made of aqueous suspensions, of isotonic saline solutions or of injectable sterile solutions which contain pharmacologically compatible dispersing agents and/or wetting agents, for example propylene glycol or butylene glycol.

The active substance can also be formulated in the form of microcapsules, where appropriate together with one or more excipients or adjuvants, or else with a polymeric matrix or with a cyclodextrin (patches, prolonged release forms).

Finally, in addition to a compound of the general formula (I), the pharmaceutical compositions according to the invention can comprise other active substances which can be employed in the treatment of the abovementioned disorders and diseases.

What is claimed is:

1. A compound which of formula (I)

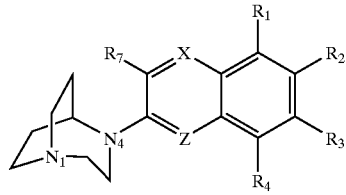

(I)

in which $R_1$, $R_2$, $R_3$ and $R_4$ each represent, independently of each other, a hydrogen or halogen atom or a nitro, amino, trifluoromethyl, cyano, hydroxyl, $(C_1-C_6)$alkyl or $(C_1-C_6)$alkoxy group, X represents
  either a nitrogen atom, in which case Z represents a group of the formula C—$R_5$ or a nitrogen atom,
  or a group of the formula C—$R_6$, in which case Z represents a nitrogen atom, $R_5$ and $R_6$ each represent, independently of each other, a hydrogen or halogen atom or a trifluoromethyl, cyano, hydroxyl, $(C_1-C_6)$alkyl or $(C_1-C_6)$alkoxy group, and $R_7$ represents a hydrogen atom or a $(C_1-C_6)$alkyl group, as a base or an acid addition salt.

2. A process for preparing compounds as claimed in claim 1, wherein 1,4-diazabicyclo[3.2.2]nonane is reacted with a heterocyclic compound of the general formula (III)

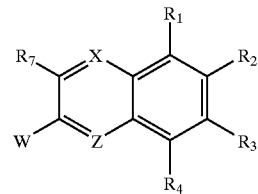

(III)

in which $R_1$, $R_2$, $R_3$, $R_4$, $R_7$, X and Z are as defined in claim 1 and W represents a halogen atom.

3. A pharmaceutical composition which comprises a compound as claimed in claim 1 combined with an excipient.

* * * * *